US008623660B2

(12) United States Patent (10) Patent No.: US 8,623,660 B2
Kraft et al. (45) Date of Patent: Jan. 7, 2014

(54) HAND-HELD TEST METER WITH PHASE-SHIFT-BASED HEMATOCRIT MEASUREMENT CIRCUIT

(75) Inventors: Ulrich Kraft, Hofheim (DE); David Elder, Inverness (GB); Mahyar Kermani, San Ramon, CA (US)

(73) Assignee: LifeScan Scotland Limited, Inverness (GB)

( * ) Notice: Subject to any disclaimer, the term of this patent is extended or adjusted under 35 U.S.C. 154(b) by 166 days.

(21) Appl. No.: 13/250,525

(22) Filed: Sep. 30, 2011

(65) Prior Publication Data

US 2013/0084589 A1 Apr. 4, 2013

(51) Int. Cl.
 G01N 33/48 (2006.01)
 G01N 33/66 (2006.01)
 G01N 27/00 (2006.01)
 C12Q 1/02 (2006.01)
 C12Q 1/54 (2006.01)

(52) U.S. Cl.
 USPC .......... 436/70; 436/63; 436/95; 436/149; 436/150; 422/73; 422/83.01; 435/14; 435/29; 204/400

(58) Field of Classification Search
 USPC ......... 436/14, 63, 70, 95, 149, 150; 422/68.1, 422/73, 82.01, 82.02; 435/14, 29; 204/400 600/365
 See application file for complete search history.

(56) References Cited

U.S. PATENT DOCUMENTS

| 4,945,313 | A |   | 7/1990 | Brilka et al. |
| 5,320,732 | A |   | 6/1994 | Nankai et al. |
| 5,642,734 | A | * | 7/1997 | Ruben et al. ................. 600/506 |
| 5,869,971 | A | * | 2/1999 | Sherman ...................... 324/439 |
| 2007/0084734 | A1 |   | 4/2007 | Roberts et al. |
| 2007/0087397 | A1 |   | 4/2007 | Kraft et al. |
| 2009/0084678 | A1 | * | 4/2009 | Joshi et al. ............... 204/403.14 |
| 2011/0089957 | A1 |   | 4/2011 | Sheppard, Jr. |
| 2013/0084590 | A1 | * | 4/2013 | Lugo Jimenez ............... 435/14 |
| 2013/0084591 | A1 | * | 4/2013 | McColl et al. ................. 435/29 |

FOREIGN PATENT DOCUMENTS

| EP | 1394545 A1 | 3/2004 |
| WO | WO 2010/049669 A1 | 5/2010 |

OTHER PUBLICATIONS

L. Shrimanth Sudheer, et al. "Microcontroller based phase meter," Journal of Instrument Soc. of India, KA, India, Mar. 2009, vol. 39 No. 1, pp. 62-64.
International Search Report, European Patent Office, Rijswijk, Netherlands, Jan. 7, 2013, re Application No. PCT/GB2012/052421.

* cited by examiner

*Primary Examiner* — Maureen Wallenhorst

(57) ABSTRACT

A hand-held test meter for use with an analytical test strip in the determination of an analyte in a bodily fluid sample includes a housing; a microcontroller block disposed in the housing; and a phase-shift-based hematocrit measurement block. The phase-shift-based hematocrit measurement block includes a signal generation sub-block, a low pass filter sub-block, an analytical test strip sample cell interface sub-block, a transimpedance amplifier sub-block, and a phase detector sub-block. In addition, the phase-shift-based hematocrit measurement block and microcontroller block are configured to measure the phase shift of a bodily fluid sample in a sample cell of an analytical test strip inserted in the hand-held test meter and the microcontroller block is configured to compute the hematocrit of the bodily fluid sample based on the measured phase shift.

21 Claims, 6 Drawing Sheets

HAND-HELD TEST METER WITH PHASE-SHIFT-BASED HEMATOCRIT MEASUREMENT CIRCUIT

BACKGROUND OF THE INVENTION

1. Field of the Invention

The present invention relates, in general, to medical devices and, in particular, to test meters and related methods.

2. Description of Related Art

The determination (e.g., detection and/or concentration measurement) of an analyte in a fluid sample is of particular interest in the medical field. For example, it can be desirable to determine glucose, ketone bodies, cholesterol, lipoproteins, triglycerides, acetaminophen and/or HbA1c concentrations in a sample of a bodily fluid such as urine, blood, plasma or interstitial fluid. Such determinations can be achieved using a hand-held test meter in combination with analytical test strips (e.g., electrochemical-based analytical test strips).

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements, of which:

DETAILED DESCRIPTION OF ILLUSTRATIVE EMBODIMENTS

Figure 1:
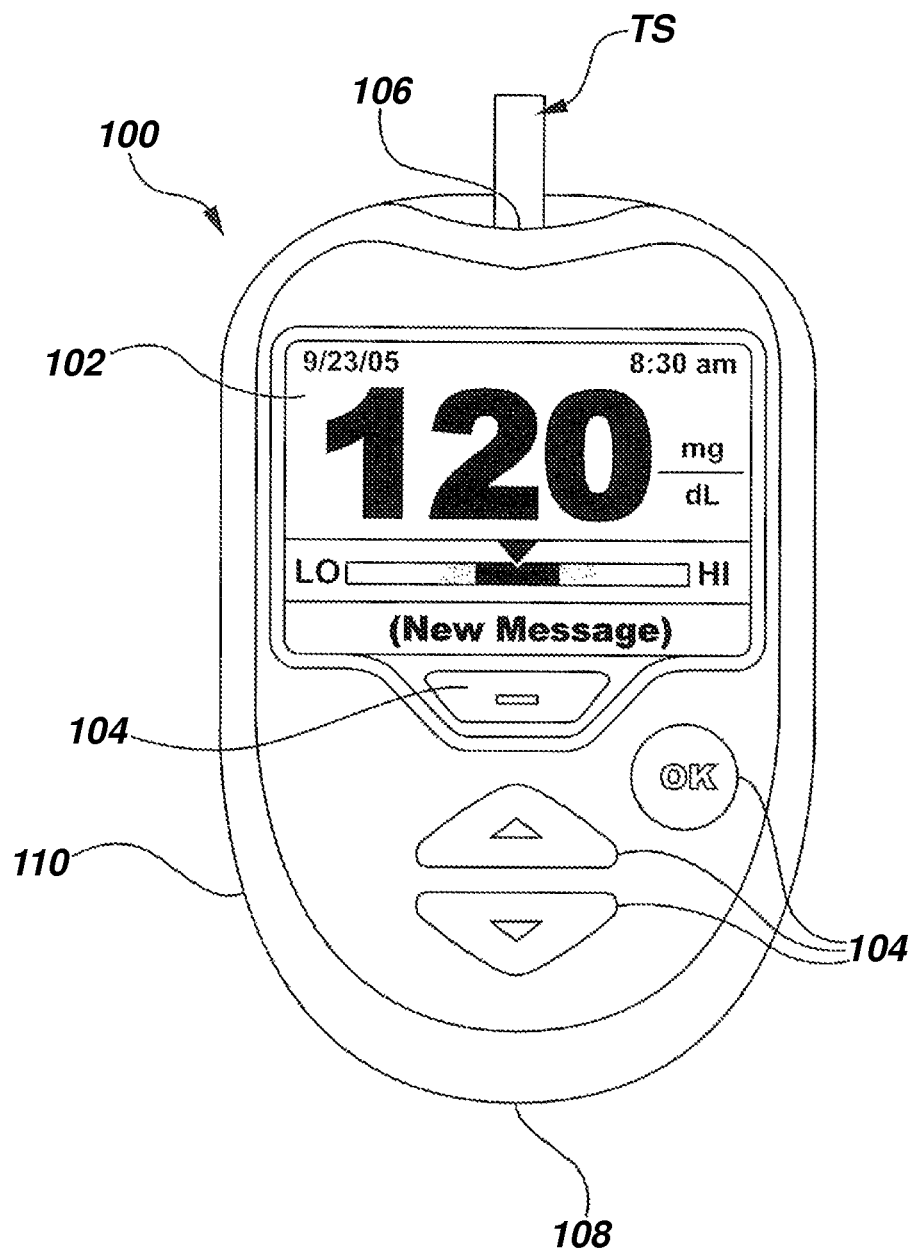
FIG. 1 is a simplified depiction of a hand-held test meter according to an embodiment of the present invention.

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

In general, hand-held test meters for use with an analytical test strip in the determination of an analyte (such as glucose) in a bodily fluid sample (i.e., a whole blood sample) according to embodiments of the present invention include a housing, a microcontroller block disposed in the housing, and a phase-shift-based hematocrit measurement block (also referred to as a phase-shift-based hematocrit circuit). In such hand-held test meters, the phase-shift-based hematocrit measurement block includes a signal generation sub-block, a low pass filter sub-block, an analytical test strip sample cell interface sub-block, a transimpedance amplifier sub-block, and a phase detector sub-block. In addition, the phase-shift-based hematocrit measurement block and microcontroller block are configured to measure the phase shift of a bodily fluid sample in a sample cell of an analytical test strip inserted in the hand-held test meter and the microcontroller block is also configured to compute the hematocrit of the bodily fluid sample based on the measured phase shift.

Hand-held test meters according to embodiments of the present invention are beneficial in that they provide improved accuracy of analyte determination (such as glucose determination) in whole blood samples by measuring the hematocrit of the whole blood sample and then employing the measured hematocrit during analyte determination.

Once one skilled in the art is apprised of the present disclosure, he or she will recognize that an example of a hand-held test meter that can be readily modified as a hand-hand test meter according to the present invention is the commercially available OneTouch® Ultra® 2 glucose meter from LifeScan Inc. (Milpitas, Calif.). Additional examples of hand-held test meters that can also be modified are found in U.S. Patent Application Publications Nos. 2007/0084734 (published on Apr. 19, 2007) and 2007/0087397 (published on Apr. 19, 2007) and in International Publication Number WO2010/049669 (published on May 6, 2010), each of which is hereby incorporated herein in full by reference.

Figure 2:
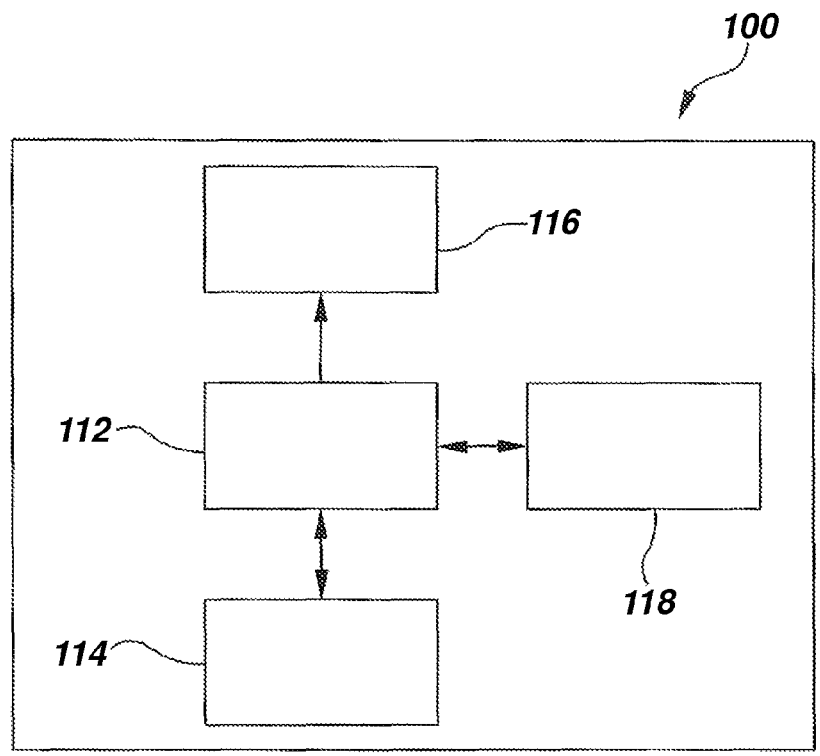
FIG. 2 is a simplified block diagram of various blocks of the hand-held test meter of FIG. 1.
Figure 3:
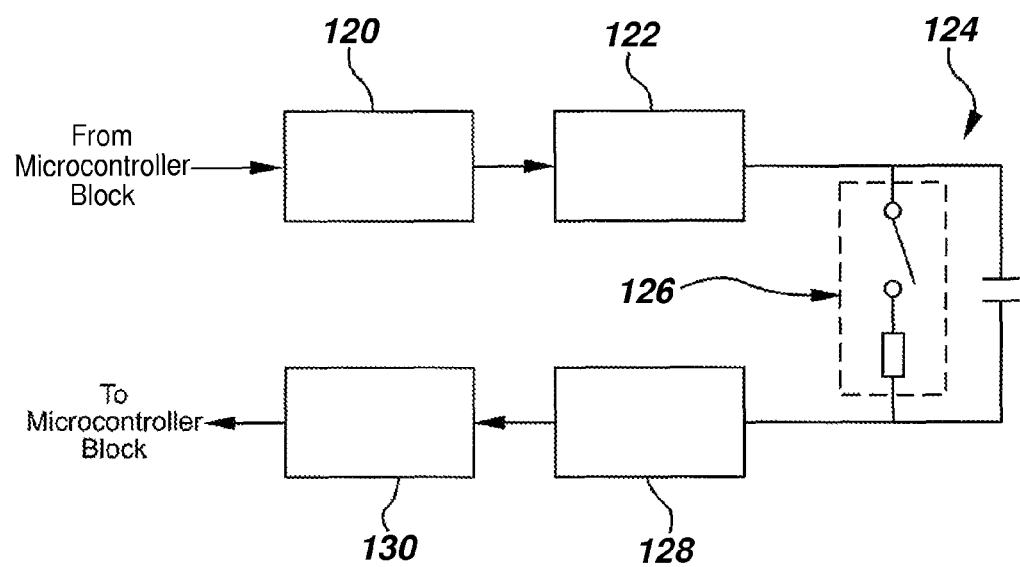
FIG. 3 is a simplified block diagram of a phase-shift-based hematocrit measurement block as can be employed in embodiments according to the present invention.
Figure 4:
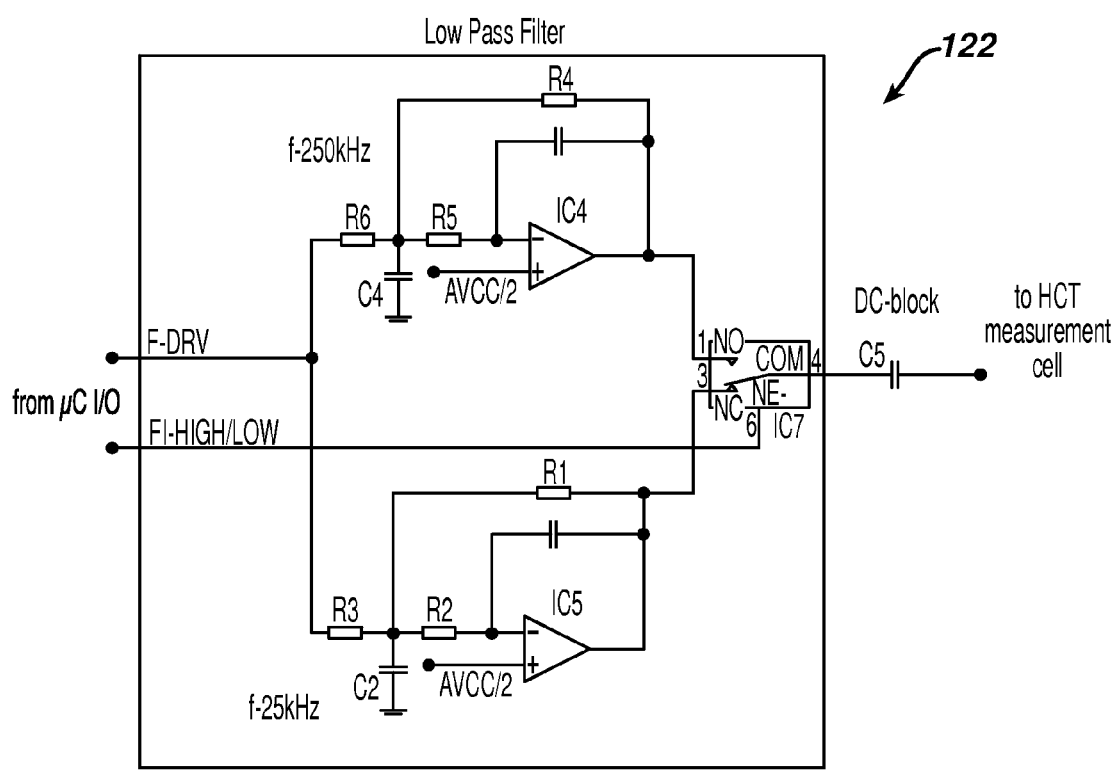
FIG. 4 is a simplified annotated schematic diagram of a dual low pass filter sub-block as can be employed in embodiments of the present invention.
Figure 5:
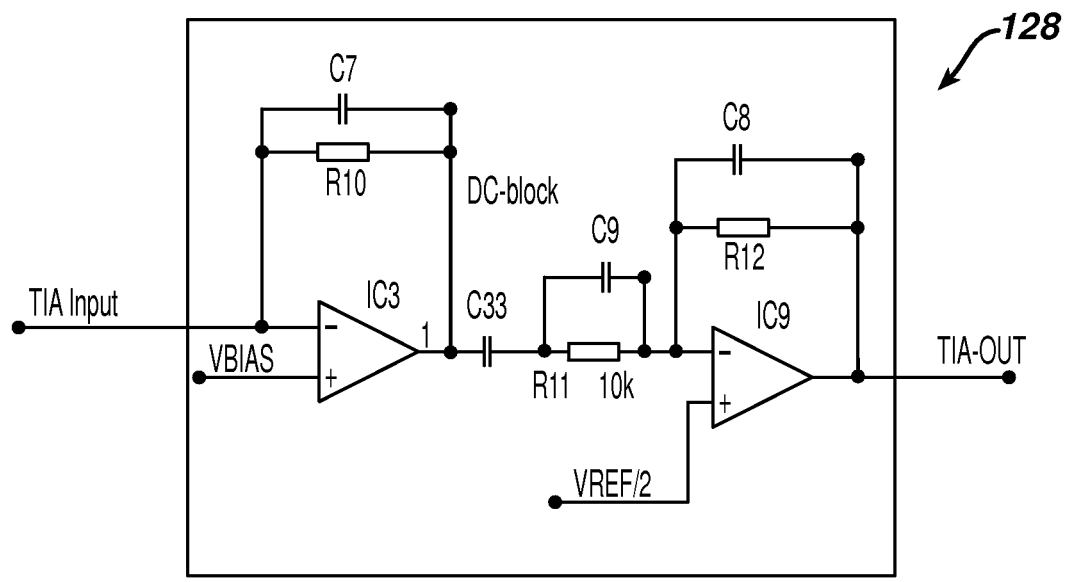
FIG. 5 is a simplified annotated schematic diagram of a transimpedance amplifier (TIA) sub-block as can be employed in embodiments of the present invention.
Figure 6:
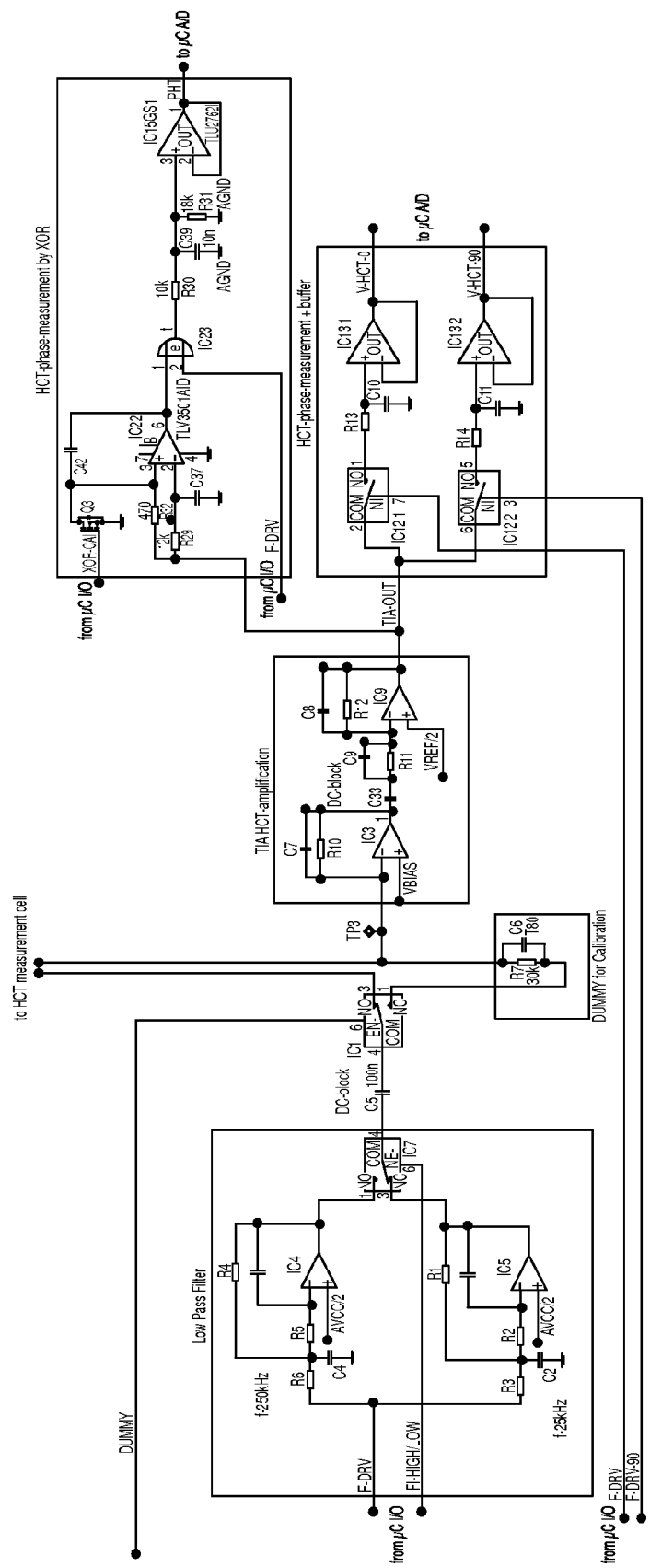
FIG. 6 is a simplified annotated schematic block diagram depicting a dual low pass filter sub-block, a calibration load sub-block, an analytical test strip sample cell interface sub-block, a transimpedance amplifier sub-block, an XOR phase shift measurement sub-block and a Quadratur DEMUX phase-shift measurement sub-block as can be employed in a phase-shift-based hematocrit measurement block of embodiments of the present invention.

FIG. 1 is a simplified depiction of a hand-held test meter 100 according to an embodiment of the present invention. FIG. 2 is a simplified block diagram of various blocks of hand-held test meter 100. FIG. 3 is a simplified combined block diagram of a phase-shift-based hematocrit measurement block of hand-held test meter 100. FIG. 4 is a simplified annotated schematic diagram of a dual low pass filter sub-block of hand-held test meter 100. FIG. 5 is a simplified annotated schematic diagram of a transimpedance amplifier sub-block of hand-held test meter 100. FIG. 6 is a simplified annotated schematic block diagram of portions of a phase-shift-based hematocrit measurement block of hand-held test meter 100.

Referring to FIGS. 1 through 6, hand-held test meter 100 includes a display 102, a plurality of user interface buttons 104, a strip port connector 106, a USB interface 108, and a housing 110 (see FIG. 1). Referring to FIG. 2 in particular, hand-held test meter 100 also includes a microcontroller block 112, a phase-shift-based hematocrit measurement block 114, a display control block 116, a memory block 118 and other electronic components (not shown) for applying a test voltage to analytical test strip (labeled TS in FIG. 1), and also for measuring an electrochemical response (e.g., plurality of test current values) and determining an analyte based on the electrochemical response. To simplify the current descriptions, the figures do not depict all such electronic circuitry.

Display 102 can be, for example, a liquid crystal display or a bi-stable display configured to show a screen image. An example of a screen image may include a glucose concentration, a date and time, an error message, and a user interface for instructing an end user how to perform a test.

Strip port connector 106 is configured to operatively interface with an analytical test strip TS, such as an electrochemical-based analytical test strip configured for the determination of glucose in a whole blood sample. Therefore, the analytical test strip is configured for operative insertion into strip port connector 106 and to operatively interface with phase-shift-based hematocrit measurement block 114 via, for example, suitable electrical contacts.

USB Interface 108 can be any suitable interface known to one skilled in the art. USB Interface 108 is essentially a passive component that is configured to power and provide a data line to hand-held test meter 100.

Once an analytical test strip is interfaced with hand-held test meter 100, or prior thereto, a bodily fluid sample (e.g., a whole blood sample) is introduced into a sample chamber of the analytical test strip. The analytical test strip can include enzymatic reagents that selectively and quantitatively transform an analyte into another predetermined chemical form. For example, the analytical test strip can include an enzymatic reagent with ferricyanide and glucose oxidase so that glucose can be physically transformed into an oxidized form.

Memory block 118 of hand-held test meter 100 includes a suitable algorithm and can be configured, along with microcontroller block 112 to determine an analyte based on the electrochemical response of analytical test strip and the hematocrit of the introduced sample. For example, in the determination of the analyte blood glucose, the hematocrit can be used to compensate for the effect of hematocrit on electrochemically determined blood glucose concentrations.

Microcontroller block 112 is disposed within housing 110 and can include any suitable microcontroller and/or microprocessor known to those of skill in the art. One such suitable microcontroller is a microcontroller commercially available from Texas Instruments, Dallas, Tex. USA and part number MSP430F5138. This microcontroller can generate a square wave of 25 to 250 kHz and a 90 degree phase-shifted wave of the same frequency and, thereby, function as a signal generation s-block described further below. MSP430F5138 also has Analog-to-Digital (ND) processing capabilities suitable for measuring voltages generated by phase shift based hematocrit measurement blocks employed in embodiments of the present invention.

Referring in particular to FIG. 3, phase-shift-based hematocrit measurement block 114 includes a signal generation sub-block 120, a low pass filter sub-block 122, an analytical test strip sample cell interface sub-block 124, an optional calibration load block 126 (within the dashed lines of FIG. 3), a transimpedance amplifier sub-block 128, and a phase detector sub-block 130.

As described further below, phase-shift-based hematocrit measurement block 114 and microcontroller block 112 are configured to measure the phase shift of a bodily fluid sample in a sample cell of an analytical test strip inserted in the hand-held test meter by, for example, measuring the phase shift of one or more high frequency electrical signals driven through the bodily fluid sample. In addition, microcontroller block 112 is configured to compute the hematocrit of the bodily fluid based on the measured phase shift. Microcontroller 112 can compute the hematocrit by, for example, employing an A/D converter to measure voltages received from a phase-detector sub-block, convert the voltages into a phase-shift and then employing a suitable algorithm or look-up table to convert the phase-shift into a hematocrit value. Once apprised of the present disclosure, one skilled in the art will recognize that such an algorithm and/or look-up table will be configured to take into account various factors such as strip geometry (including electrode area and sample chamber volume) and signal frequency.

It has been determined that a relationship exists between the reactance of a whole blood sample and the hematocrit of that sample. Electrical modeling of a bodily fluid sample (i.e., a whole blood sample) as parallel capacitive and resistive components indicates that when an alternating current (AC) signal is forced through the bodily fluid sample, the phase shift of the AC signal will be dependent on both the frequency of the AC voltage and the hematocrit of the sample. Moreover, modeling indicates that hematocrit has a relatively minor effect on the phase shift when the frequency of the signal is in the range of approximately 10 kHz to 25 kHz and a maximum effect on the phase shift when the frequency of the signal is in the range of approximately 250 kHz to 500 KHz. Therefore, the hematocrit of a bodily fluid sample can be measured by, for example, driving AC signals of known frequency through the bodily fluid sample and detecting their phase shift. For example, the phase-shift of a signal with a frequency in the range of 10 kHz to 25 kHz can be used as a reference reading in such a hematocrit measurement while the phase shift of a signal with a frequency in the range of 250 kHz to 500 kHz can be used as the primary measurement.

Referring to FIGS. 3 through 6 in particular, signal generation sub-block 120 can be any suitable signal generation block and is configured to generate a square wave (0V to Vref) of a desired frequency. Such a signal generation sub-block can, if desired, be integrated into microcontroller block 112.

The signal generated by signal generation sub-block 120 is communicated to dual low pass filter sub-block 122, which is configured to convert the square wave signal to a sine wave signal of a predetermined frequency. The dual LPF of FIG. 4 is configured to provide both a signal of a first frequency (such as a frequency in the range of 10 kHz to 25 kHz) and a signal of a second frequency (such as a frequency in the range of 250 kHz to 500 kHz) to the analytical test strip sample cell interface sub-block and an analytical test strips' sample chamber (also referred to as the HCT measurement cell). Selection of the first and second frequency is accomplished using switch IC7 of FIG. 4. The dual LPF of FIG. 4 includes employs two suitable operational amplifiers (IC4 and IC5) such as the operational amplifier available from Texas Instruments, Dallas, Tex., USA as high-speed, voltage feedback, CMOS operational amplifier part number OPA354.

Referring to FIG. 4, F-DRV represents a square wave input of either a low or high frequency (e.g., 25 kHz or 250 kHz) and is connected to both IC4 and IC5. Signal Fi-HIGH/LOW (from the microcontroller) selects the output of dual low pass filter sub-block 122 via switch IC7. C5 in FIG. 4 is configured to block the operating voltage of dual low pass filter sub-block 122 from the HCT measurement cell.

Although a specific dual LPF is depicted in FIG. 4, dual low pass filter sub-block 122 can be any suitable low pass filter sub-block known to one skilled in the art including, for example, any suitable multiple feedback low pass filter, or a Sallen and Key low pass filter.

The sine wave produced by low pass filter sub-block 122 is communicated to analytical test strip sample cell interface sub-block 124 where it is driven across the sample cell of the analytical test strip (also referred to as an HCT measurement cell). Analytical test strip sample cell interface block 124 can be any suitable sample cell interface block including, for example, an interface block configured to operatively interface with the sample cell of the analytical test strip via first electrode and second electrodes of the analytical test strip disposed in the sample cell. In such a configuration, the signal can be driven into the sample cell (from the low pass filter sub-block) via the first electrode and picked-up from the sample cell (by the transimpedance amplifier sub-block) via the second electrode as depicted in FIG. 6.

The current produced by driving the signal across the sample cell is picked-up by transimpedance amplifier sub-block 128 and converted into a voltage signal for communication to phase detector sub-block 130.

Transimpedance sub-block 128 can be any suitable transimpedance sub-block known to one skilled in the art. FIG. 5 is a simplified annotated schematic block diagram of one such transimpedance amplifier sub-block (based on two OPA354 operational amplifiers, IC3 and IC9). The first stage of TIA sub-block 128 operates at, for example, 400 mV, which limits the AC amplitude to +/−400 mV. The second stage of TIA sub-block 128 operates at Vref/2, a configuration which enables the generation of an output of the full span of the microcontroller ND inputs. C9 of TIA sub-block 128 serves as a blocking component that only allows an AC sine wave signal to pass.

Phase detector sub-block 130 can be any suitable phase detector sub-block that produces either a digital frequency that can be read back by microcontroller block 112 using a capture function, or an analog voltage that can be read back by microcontroller block 112 using an analog to digital converter. FIG. 6 depicts a schematic that includes two such phase detector sub-blocks, namely an XOR phase detector (in the upper half of FIG. 6 and including IC22 and IC23) and a Quadrature DEMUX phase detector (in the lower half of FIG. 6 and including IC12 and IC13).

FIG. 6 also depicts a calibration load sub-block 126 that includes a switch (IC16) and a dummy load R7 and C6. Calibration load sub-block 126 is configured for the dynamic measurement of a phase offset for the known phase shift of zero degrees produced by resistor R7, thus providing a phase offset for use in calibration. C6 is configured to force a predetermined slight phase shift, e.g. to compensate for phase delays caused by parasitic capacities in the signal traces to the sample cell, or for phase delays in the electrical circuits (LPF and TIA).

The Quadrature DEMUX phase detector circuit of FIG. 6 includes two portions, one portion for a resistive part of the incoming AC signal and one portion for the reactive portion of the incoming AC signal. Use of such two portions enables the simultaneous measurement of both the resistive and reactive portion of the AC signal and a measurement range that covers 0 degrees to 360 degrees. The Quadrature DEMUX circuit of FIG. 6 generates two separate output voltages. One of these output voltages represents the "in phase measurement" and is proportional to the "resistive" part of the AC signal, the other output voltage represents the "Quadrature Measurement" and is proportional to the "reactive part of the signal. The phase shift is calculated as:

$$\phi = \tan^{-1}(V_{QUAD-PHASE}/V_{IN-PHASE})$$

Such a Quadrature DEMUX phase detector circuit can also be employed to measure the impedance of a bodily fluid sample in the sample cell. It is hypothesized, without being bound, that the impedance could be employed along with the phase-shift, or independently thereof, to determine the hematocrit of the bodily sample. The amplitude of a signal forced through the sample cell can be calculated using the two voltage outputs of the Quadrature DEMUX circuit as follows:

$$\text{Amplitude} = \text{SQR}((V_{QUAD-PHASE})^2 + (V_{IN-PHASE})^2)$$

This amplitude can then be compared to an amplitude measured for the known resistor of calibration load block 126 to determine the impedance.

The XOR phase detector portion has a measurement range of 0° to 180°, or alternatively a measurement range of −90° to +90°, depending whether the "Square wave input from μC" is in phase to the sine wave or is set to a 90° phase shift. The XOR phase detector produces an output frequency that is always double the input frequency, however the duty cycle varies. If both inputs are perfectly in phase, the output is LOW, if both inputs are 180° shifted the output is always HIGH. By integrating the output signal (e.g. via a simple RC element) a voltage can be generated that is directly proportional to the phase shift between both inputs.

Once apprised of the present disclosure, one skilled in the art will recognize that phase detector sub-blocks employed in embodiments of the present invention can take any suitable form and include, for example, forms that employ rising edge capture techniques, dual edge capture techniques, XOR techniques and synchronous demodulation techniques.

Since low pass filter sub-block 122, transimpedance amplifier sub-block 128 and phase detector sub-block 130 can introduce a residual phase shift into phase-shift-based hematocrit measurement block 114, calibration load block 126 can be optionally included in the phase-shift-based hematocrit measurement block. Calibration load block 126 is configured to be essentially resistive in nature (for example a 33 k-ohm load) and, therefore, induces no phase shift between excitation voltage and generated current. Calibration load block 126 is configured to be switched in across the circuit to give a "zero" calibration reading. Once calibrated, the hand-held test meter can measure the phase shift of a bodily fluid sample, subtract the "zero" reading to compute a corrected phase shift and subsequently compute the bodily sample hematocrit based on the corrected phase shift.

Figure 7:
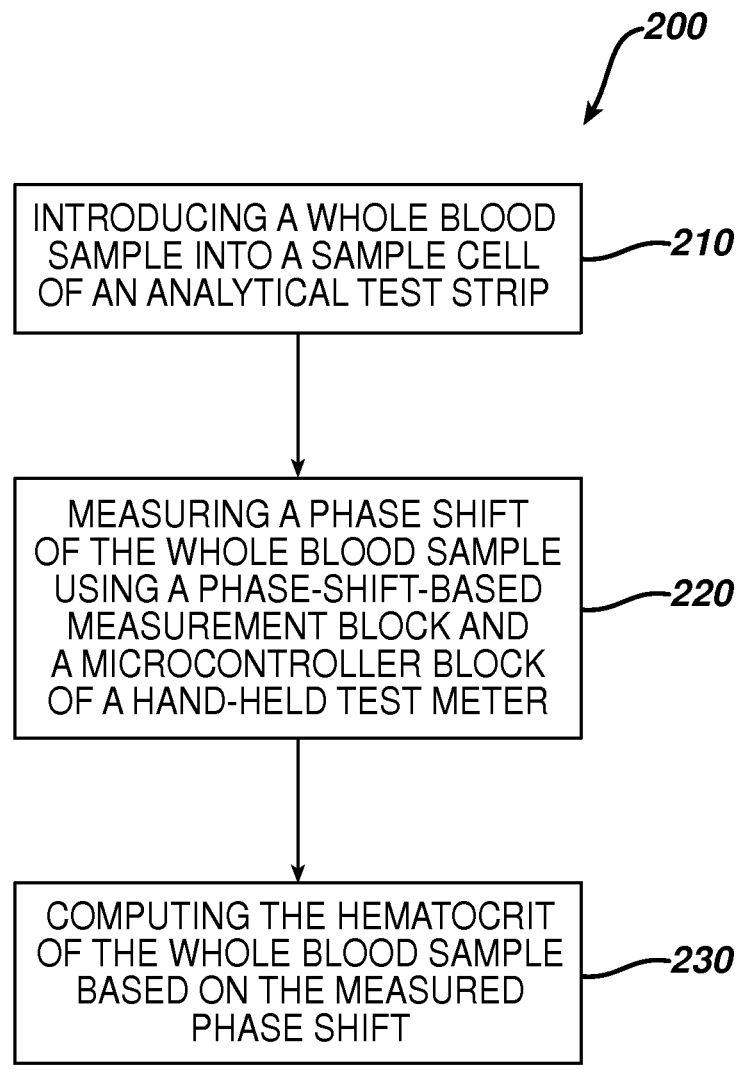
FIG. 7 is a flow diagram depicting stages in a method for employing a hand-held test meter according to an embodiment of the present invention.

FIG. 7 is a flow diagram depicting stages in a method 200 for employing a hand-held test meter and analytical test strip (e.g., an electrochemical-based analytical test strip). Method 200, at step 210, includes introducing a whole blood sample into a sample cell of the analytical test strip.

At step 220, a phase shift of the whole blood sample in the sample cell is measured using a phase-shift-based measurement block and a microcontroller block of a hand-held test meter. Method 200 further includes computing the hematocrit of whole blood sample based on the measured phase shift using the microcontroller block (see step 230 of FIG. 7).

Once apprised of the present disclosure, one skilled in the art will recognize that methods according to embodiments of the present invention, including method 200, can be readily modified to incorporate any of the techniques, benefits and characteristics of hand-held test meters according to embodiments of the present invention and described herein. For example, if desired, an analyte in the introduced bodily fluid sample using the analytical test strip, hand-held test meter and computed hematocrit.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the inven-

What is claimed is:

1. A hand-held test meter for use with an analytical test strip in the determination of an analyte in a bodily fluid sample, the hand-held test meter comprising:
   a housing;
   a microcontroller block disposed in the housing; and
   a phase-shift-based hematocrit measurement block disposed in the housing, the phase-shift-based hematocrit measurement block including, in series order:
      a signal generation sub-block configured to generate at least a first electrical signal of a first frequency is in the range of 10 kHz to 25 kHz and a second electrical signal of a second frequency in the range of 250 kHz to 500 kHz;
      a low pass filter sub-block;
      an analytical test strip sample cell interface sub-block;
      a transimpedance amplifier sub-block; and
      a phase detector sub-block,
   wherein the phase-shift-based hematocrit measurement block and microcontroller block are configured to measure the phase shift of a bodily fluid sample in a sample cell of an analytical test strip inserted in the hand-held test meter using both the first signal of the first frequency and the second signal of the second frequency,
   wherein the phase-shift-based hematocrit measurement block and microcontroller block are configured such that the signal of the first frequency is employed as a reference signal during the measurement of the phase shift of a bodily fluid sample; and
   wherein the microcontroller block is configured to compute the hematocrit of the bodily fluid based on the measured phase shift.

2. The hand-held test meter of claim 1 wherein the bodily fluid sample is a whole blood sample.

3. The hand-held test meter of claim 1 wherein the phase detector sub-block is configured as a rising edge capture phase detector.

4. The hand-held test meter of claim 1 wherein the phase detector sub-block is configured as a dual edge capture phase detector.

5. The hand-held test meter of claim 1 wherein the phase detector sub-block is configured as an XOR phase detector.

6. The hand-held test meter of claim 1 wherein the phase detector sub-block is configured as a synchronous modulation phase detector.

7. The hand-held test meter of claim 1 further including a calibration load sub-block configured in parallel with the analytical test strip sample cell interface sub-block and to provide a phase offset for use in calibration.

8. The hand-held test meter of claim 1 wherein the phase-shift-based hematocrit measurement block and microcontroller block are configured to measure the phase shift of a bodily fluid sample in a sample cell of an analytical test strip inserted in the hand-held test meter by forcing a signal of known frequency through the bodily fluid sample and measuring the phase-shift of the signal.

9. The hand-held test meter of claim 1 wherein the signal generation sub-block is integrated with the microcontroller block.

10. The hand-held test meter of claim 1 wherein the analytical test strip sample cell interface sub-block is configured to operatively interface with the sample cell of the analytical test strip via a first electrode and a second electrode of the analytical test strip disposed in the sample cell.

11. The hand-held test meter of claim 1 wherein the analytical test strip is an electrochemical-based analytical test strip configured for the determination of glucose in a whole blood sample.

12. The hand-held test meter of claim 1 wherein the phase detector sub-block is configured as a Quadratur DEMUX phase detector.

13. A method for employing a hand-held test meter and analytical test strip, the method comprising:
   inserting an analytical test strip into a hand-held test meter;
   introducing a whole blood sample into a sample cell of the analytical test strip;
   measuring a phase shift of the whole blood sample in the sample cell using a phase-shift-based hematocrit measurement block and a microcontroller block of the hand-held test meter;
   computing the hematocrit of whole blood sample based on the measured phase shift using the microcontroller block, and
   wherein the phase-shift-based hematocrit measurement block and microcontroller block are configured to measure the phase shift of the whole blood sample using a signal of a first frequency in the range of 10 kHz to 25 kHz as a reference signal and a second signal of a second frequency in the range of 250 kHz to 500 kHz.

14. The method of claim 13 further including:
   determining an analyte in the introduced whole blood sample using the analytical test strip, hand-held test meter and computed hematocrit.

15. The method of claim 14 wherein the analytical test strip is an electrochemical-based analytical test strip and the analyte is glucose.

16. The method of claim 13 wherein the measuring step includes measuring the phase shift with a phase-shift based measurement circuit block disposed within the hand-held test meter that includes, in series order:
   a signal generation sub-block;
   a low pass filter sub-block;
   an analytical test strip sample cell interface sub-block;
   a transimpedance amplifier sub-block; and
   a phase detector sub-block.

17. The method of claim 16 wherein the phase detector sub-block is configured as a rising edge capture phase detector.

18. The method of claim 16 wherein the phase detector sub-block is configured as a dual edge capture phase detector.

19. The method of claim 16 wherein the phase detector sub-block is configured as an XOR phase detector.

20. The method of claim 16 wherein the phase detector sub-block is configured as a synchronous modulation phase detector.

21. The method of claim 16 wherein the phase detector sub-block is configured as a Quadratur DEMUX phase detector.

* * * * *